United States Patent [19]

Kambin

[11] Patent Number: 5,630,816
[45] Date of Patent: May 20, 1997

[54] DOUBLE BARREL SPINAL FIXATION SYSTEM AND METHOD

[76] Inventor: Parviz Kambin, 239 Chester Rd., Devon, Pa. 19333

[21] Appl. No.: 431,842

[22] Filed: May 1, 1995

[51] Int. Cl.⁶ .................................................. A61B 17/56
[52] U.S. Cl. ................................................. 606/61; 606/60
[58] Field of Search ............................... 606/61, 62, 63, 606/64

[56] References Cited

U.S. PATENT DOCUMENTS

| | | | |
|---|---|---|---|
| 4,257,409 | 3/1981 | Bacal et al. | 128/69 |
| 4,269,178 | 5/1981 | Keene | 128/69 |
| 4,274,401 | 6/1981 | Miskew | 128/69 |
| 4,409,968 | 10/1983 | Drummond | 606/61 |
| 4,567,884 | 2/1986 | Edwards | 128/69 |
| 4,641,636 | 2/1987 | Cotrel | 128/69 |
| 4,815,453 | 3/1989 | Cotrel | 128/69 |
| 5,005,562 | 4/1991 | Cotrel | 128/69 |
| 5,007,909 | 4/1991 | Rogozinski | 606/61 |
| 5,030,220 | 7/1991 | HoWland | 606/61 |
| 5,074,864 | 12/1991 | Cozad et al. | 606/54 |
| 5,102,412 | 4/1992 | Rogozinski | 606/61 |
| 5,112,332 | 5/1992 | Cozad et al. | 606/61 |
| 5,116,334 | 5/1992 | Cozad et al. | 606/61 |
| 5,129,900 | 7/1992 | Asher et al. | 606/61 |
| 5,147,359 | 9/1992 | Cozad et al. | 606/61 |
| 5,147,360 | 9/1992 | Dubousset | 606/61 |
| 5,154,718 | 10/1992 | Cozad et al. | 606/61 |
| 5,176,679 | 1/1993 | Lin | 606/61 |
| 5,181,917 | 1/1993 | Rogozinski | 606/61 |
| 5,196,014 | 3/1993 | Lin | 606/61 |
| 5,201,734 | 4/1993 | Cozad et al. | 606/62 |
| 5,242,445 | 9/1993 | Ashman | 606/61 |
| 5,246,442 | 9/1993 | Ashman et al. | 606/61 |
| 5,257,994 | 11/1993 | Lin | 606/61 |
| 5,281,222 | 1/1994 | Allard et al. | 606/54 |
| 5,282,801 | 2/1994 | Sherman | 606/61 |
| 5,330,473 | 7/1994 | Howland | 606/61 |
| 5,330,474 | 7/1994 | Lin | 606/61 |
| 5,346,493 | 9/1994 | Stahurski et al. | 606/61 |
| 5,413,576 | 5/1995 | Rivard | 606/61 |

FOREIGN PATENT DOCUMENTS

| | | |
|---|---|---|
| 93202825 | 10/1993 | European Pat. Off. . |
| 0578320A1 | 1/1994 | European Pat. Off. . |
| WO94/00062 | 1/1994 | WIPO . |

OTHER PUBLICATIONS

Universal Instrumentation (CD) For Spinal Surgery (Dr. Cotrel/Dr. Dubousset) (Data Sheet).
GDLH Posterior Spinal System by Danek (Brochure).
MASS System Brochure: Multiple Axial Stabilization System —Anterior Posterior Spinal Fixation.
Spinal Instrumentation: Editors Howard S. and and Jerome M. Cotler "Isola Spinal Implant System: Principles, Design, and Applications".
Tome I: Presentation of C.D. Instrumentation: Catalog/Technical Surgical Procedures (Includes: Volumes I–IV).

*Primary Examiner*—Michael Buiz
*Assistant Examiner*—Mark S. Leonardo
*Attorney, Agent, or Firm*—James W. Pravel

[57] ABSTRACT

A double barrel adjustable clamping system adaptable for use with laminar hooks and pedicular bolts for use by a surgeon for reduction and fixation of a spinal column is disclosed which provides a rigid construct and is independent from the rod system thereby simplifying the surgical installation thereof. Also disclosed are multi-piece round and quadrilateral rod systems which are separated by novel adjustable cross bar assemblies.

24 Claims, 6 Drawing Sheets

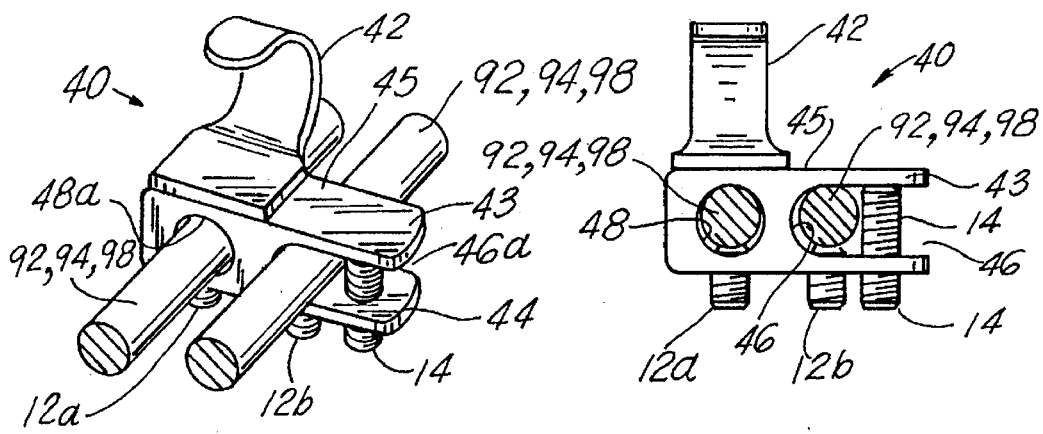
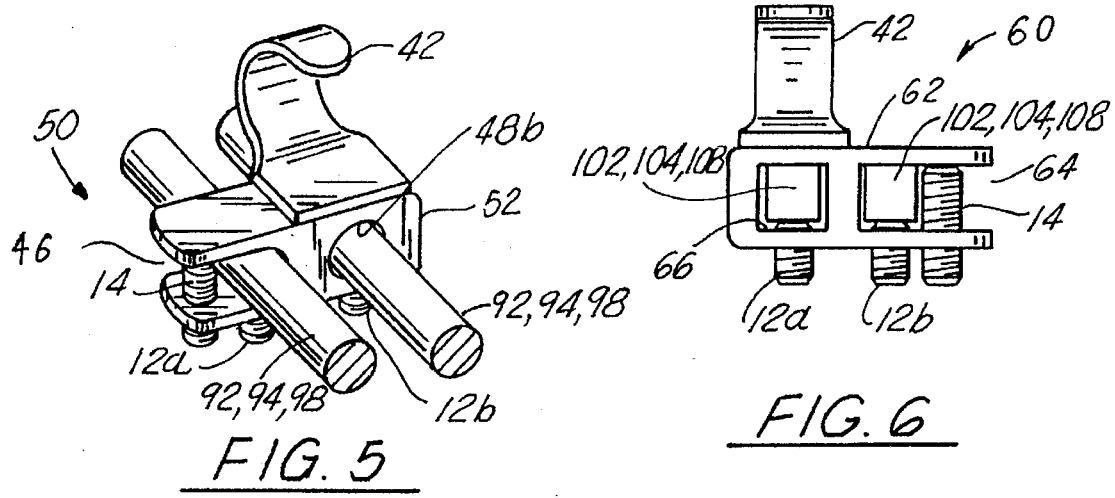
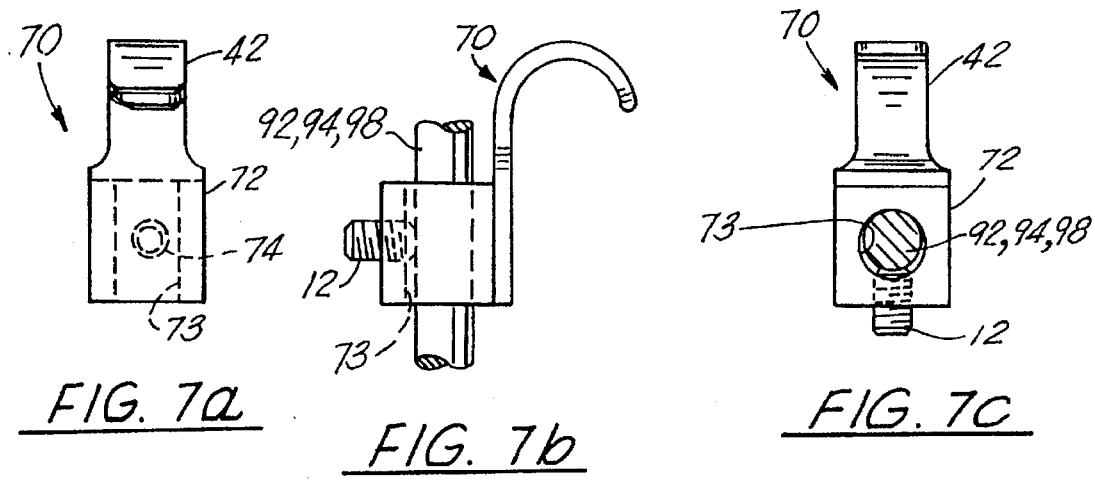

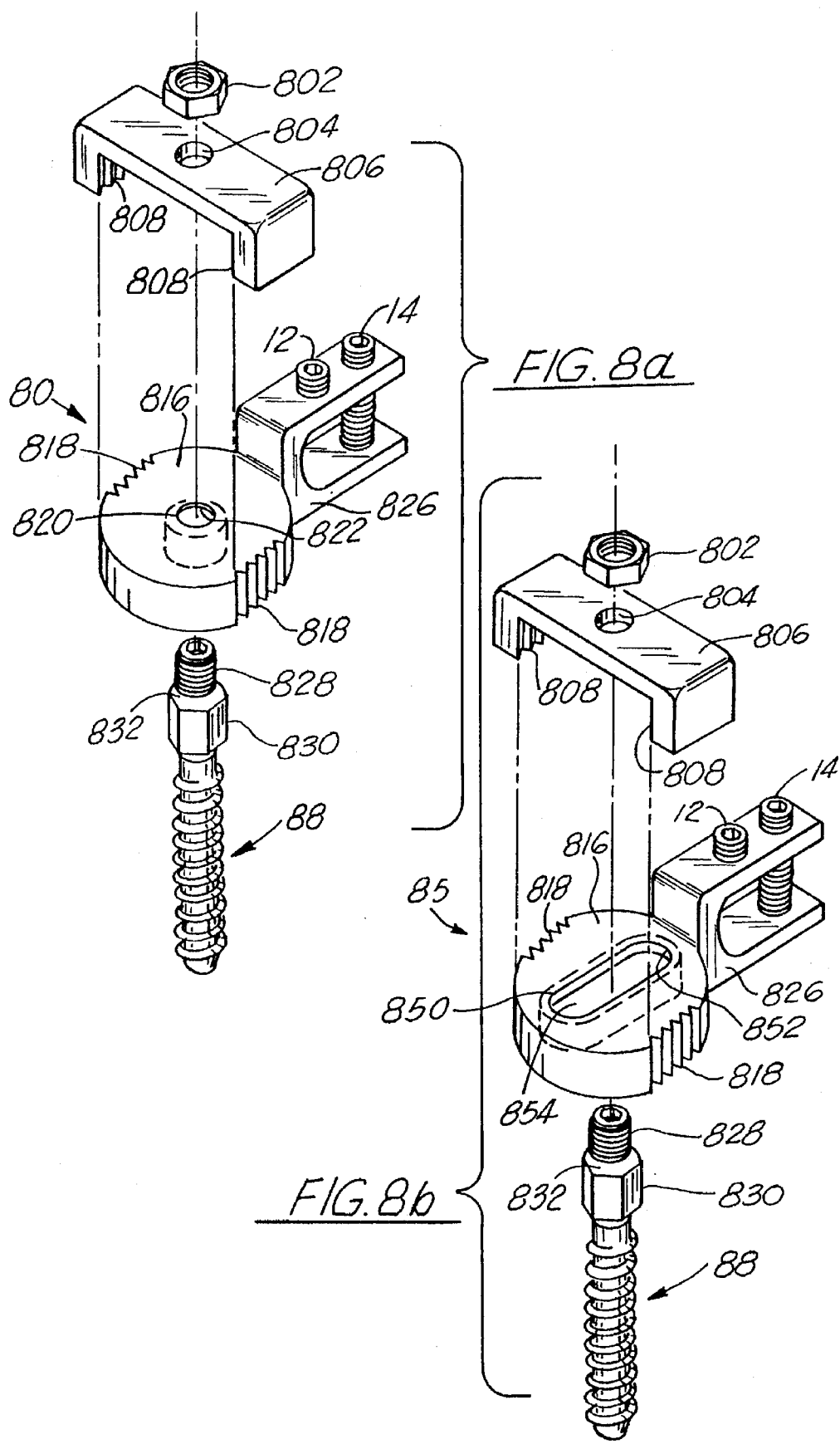

DOUBLE BARREL SPINAL FIXATION SYSTEM AND METHOD

BACKGROUND OF THE INVENTION

The present invention relates to the field of spinal correction devices. More specifically, the present invention is directed to a double barrel spinal fixation system and method that allow an operating surgeon to construct a rigid laminal claw across one or more vertebrae and provide subsequent independent reduction and fixation of a spinal deformity.

The use of spinal fixation systems is known. Such systems are used to correct spinal deformities such as: kyphosis, lordosis, hemivertebra, spondylolisthesis, scoliosis and others. Kyphosis is a sharp, angular rearward curvature. Lordosis is a forward accentuation of the cervical or lumbar regions beyond physiological levels. Hemivertebra is a developmental error in the spine caused by lack of formation of a vertebral body growth center which results in the production of wedge-shaped vertebrae or one-half of a vertebra. Spondylolisthesis is a spinal deformity in which a vertebral body with the vertebral column above it subluxes or glides forward on the vertebral body below. Scoliosis is characterized by a lateral curvature of a segment of the spine from the normally straight midline position. Other causes of spinal deformities include, but are not limited to, fractured vertebral bodies or dislocated spinal segments. Spinal fixation systems are also used to correct spinal instability. Primary instability may be acute, for example, as caused by trauma; or may be chronic, for example, as caused by degeneration or by a tumor. Secondary instability may be caused by resection, for example, by a facetectomy. Secondary instability may also be caused by overload, for example, by a misalignment or from stress concentrations.

Many existing spinal fixation systems include rod and hook components used for reduction and fixation of the spinal column. However, the existing systems require the assembly of many different intricate components that ultimately cause the surgical procedure to be complicated and unnecessarily delayed.

For example, U.S. Pat. No. 5,102,412 to Rogozinski shows a spinal rod system and method for instrumenting the spine in the treatment of spinal abnormalities. The system comprises many intricate parts. Such parts include U-shaped screw couplers for use with pedicular screws. The screw couplers are assembled with cross bars and set screws. The laminar clawing configuration requires the additional assembly of a hook bar and a set screw. Another example of spinal instrumentation is known as the Multiple Axial Stabilization System (MASS). This system uses open hooks and cable hooks. Clawing of lamina is accomplished by interconnecting either cable hooks with open hooks, or by interconnecting a pair of cable hooks. A longitudinal rod can subsequently be inserted into the groove in the open slot outside of the open hook. Provided absolute alignment with the groove is established, a sleeve can be positioned outside the rod and integral with the open hook to secure the hook to the rod. It has been found in practice that it is often cumbersome to align the rod with the groove in the clamp. The improper alignment between the rod and the groove can cause the insertion of the sleeve into the hook to be difficult. In addition, the cabling system is not sufficiently rigid to provide rotational stability.

The Isola spinal implant system is a further example of spinal instrumentation and is described in Spinal Instrumentation, pp. 324–351 (1992). The Isola system uses anchor components consisting of screws, posts, hooks and wires. Closed body and open body hooks are used. The anchors, and in particular, the hooks, are used to interconnect longitudinal rods to achieve the desired correction of spinal deformity about the sagittal plane. The hooks are placed in operative association with selected lamina while simultaneously interconnecting the longitudinal rod members.

Similarly, the Correl-Dubousset Instrumentation includes closed and open hook bodies. The hooks are used as anchor points to interconnect a flexible rod. A closed body hook and an open body hook may be used to span one or more lamina but such an installation is still integral to the total longitudinal rod component and does not allow an independent clawing of the selected lamina.

It is desirable to have a device that will allow an operating surgeon to construct a rigid laminal clamp that is independent of the rod system. The device should allow the surgeon to be able to concentrate upon the task of clawing one or multiple lamina without having to simultaneously coordinate the installation of the rod system. The device should also be easy to assemble and should provide torsional stability to correct rotational deformity of the spine. The device should be adaptable for use with pedicular bolts and with laminar hooks. The device should also be easy to install by allowing the surgeon to readily insert the longitudinal rod into the slot of the clamp and thereafter to secure the longitudinal rod when it is in the correct position.

SUMMARY OF THE INVENTION

The present invention provides a new and improved system and method for constructing a rigid laminal claw that is independent of the rod system. The clawing action may include a single lamina process or may include several lamina segments. When the clawing action is completed, the operating surgeon can proceed with the installation of secondary rods to effect the desired reduction and fixation of the spinal deformity.

In certain embodiments, the present invention is directed to a method of constructing a rigid laminal claw system which is independent of the spinal rod system and comprises the steps of: (a) surgically exposing the spine posteriorly, (b) clawing single or multiple lamina by interconnecting at least two clawing apparatus, (c) reducing and fixating the deformity of the spine by interconnecting the at least two clawing apparatus.

The present invention is readily adaptable to be used with both laminar claw engagements and to pedicular attachments with pedicular screws. The device is modular in configuration which allows the operating surgeon flexibility during the surgical installation procedure. The appropriate modular component of the invention can be implemented as needed at the appropriate time during the installation.

In another certain embodiment of the present invention a surgically implantable spinal fixation system is shown which comprises a body member having two parallel faces and an orifice therethrough which is adapted to receive a longitudinal rod member. The rod member is typically circular or quadrilateral in cross section. During the surgical installation the orifice is positioned generally along the spinal axis. The body member also has a slot that is positioned along at least one end along the spinal axis whereby a second rod member can easily be inserted into the slot from one end of the body. A laminar hook member is attached to the outer surface of one leg member. One leg member includes a threaded hole adapted to receive a threaded set screw. The set screw extends through the leg member and engages the outer surface of the rod member. The leg member also includes a second threaded hole adapted to receive a second set screw. The second set screw extends through the first leg member and engages the outer surface of the second rod member. The first leg member also includes a threaded hole adapted to receive a third set screw whereby the third threaded member extends through the first leg member and extends along at least one side of the second rod member.

The engagement between the rod members and the set screw members provides a secure and stable overall interface between the clamping members and the rod system. The secure overall interface provides desired torsional strength to the resulting spinal fixation assembly.

In addition, this invention provides the operating surgeon with the advantage of being able to successfully seat the rod member securely into the clamp slot with relative ease. The slots provided on the present inventive clamp members typically are wider across than the cross section of the rod to be inserted therein. It becomes a relatively simple matter for the surgeon to align the rod within the slot in which the appropriate set screw can be rotated into position to secure the rod within the rod slot. After the rod has been secured within the slot, the appropriate set screw can be rotated into position to bear against the side of the rod member.

An additional advantage of the present invention is that the modular components which comprise the system are relatively few. As a result, the system is less complicated, requiring a smaller inventory of parts to create a fully functional spinal fixation system.

Another advantage of the present invention is that the slotted pedicular bolt clamp allows the surgeon to position the pedicular bolt clamp to the pedicular bolt in a wide range of different positions. The slotted pedicular bolt clamp may be rotated and repositioned laterally relative to the spinal axis to provide the optimum alignment of the clamp slot to the longitudinal rod member.

Yet further, because the installation of the present invention is simplified for the surgeon, the total time required for surgical installation is reduced. In practice, a patient may indeed experience stress because of prolonged exposure to invasive surgery. The reduction in the time required for surgery provided by the present invention benefits the patient by reducing the patient's exposure to the corresponding amount of time and surgical related stress.

BRIEF DESCRIPTION OF THE DRAWINGS

The foregoing and other features of the invention will become more apparent upon a consideration of the following description taken with the accompanying drawings, wherein:

FIG. 4 is a perspective view of a certain embodiment of the right-hand double barrel laminar hook;

FIG. 4a is a bottom view of the right-hand double barrel laminar hook shown in FIG. 4;

FIG. 5 is a perspective view of a certain embodiment of the left-hand double barrel laminar hook;

FIG. 6 is a bottom view of a certain embodiment of the left-hand double barrel laminar hook configured to accommodate quadrilateral shaped rods;

FIG. 7a illustrates a front view of a certain embodiment of the single barrel laminar hook;

FIG. 7b illustrates a side view of a certain embodiment of the single barrel laminar hook;

FIG. 7c illustrates a bottom view of a certain embodiment of the single barrel laminar hook;

FIG. 8a is an exploded view of a certain embodiment of the pedicular bolt clamp and a corresponding pedicular bolt;

FIG. 8b is an exploded view of a certain embodiment of the slotted pedicular bolt clamp and a corresponding pedicular bolt;

FIG. 11b shows a detail of one end of the adjustable cross bar assembly shown in FIG. 11a;

FIG. 12b shows a detail of one end of the turnbuckle cross bar assembly shown in FIG. 12a.

SUMMARY OF THE INVENTION

Spinal Fixation System

Figure 1:
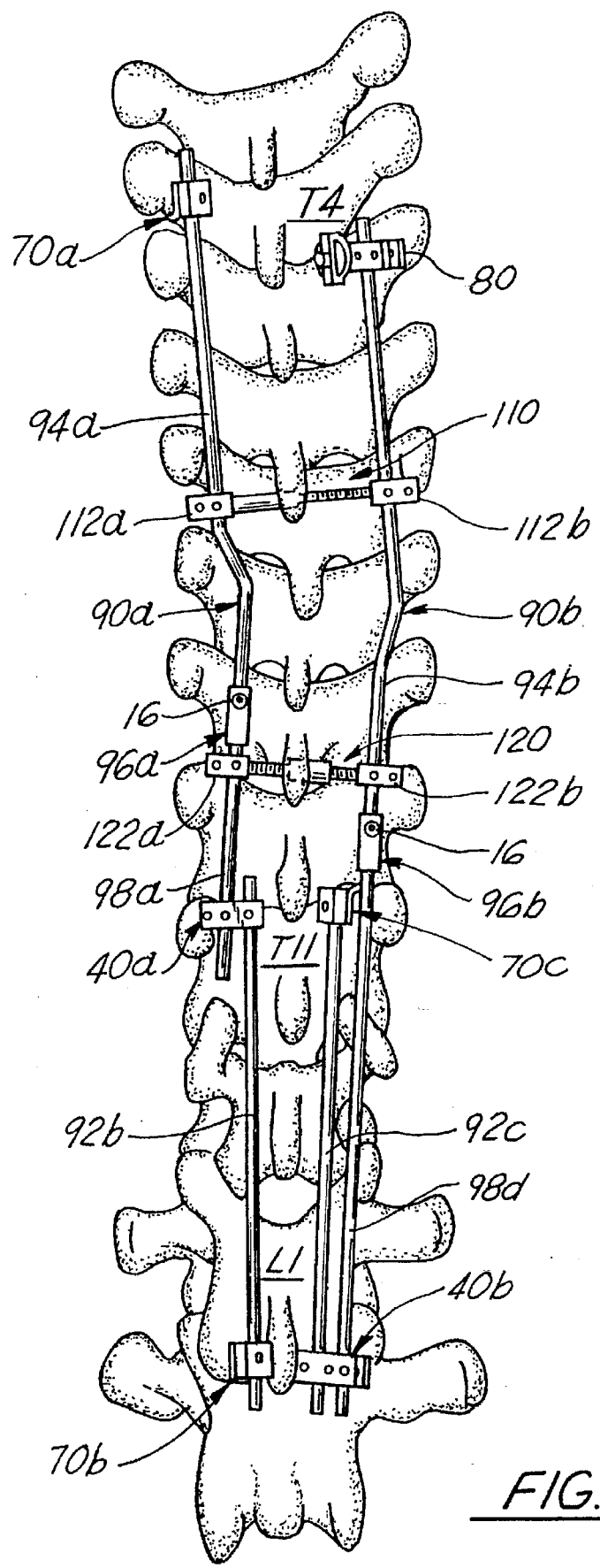
FIG. 1 is a posterior view of a spinal column with a certain embodiment of the present invention surgically installed thereon
Figure 11A:
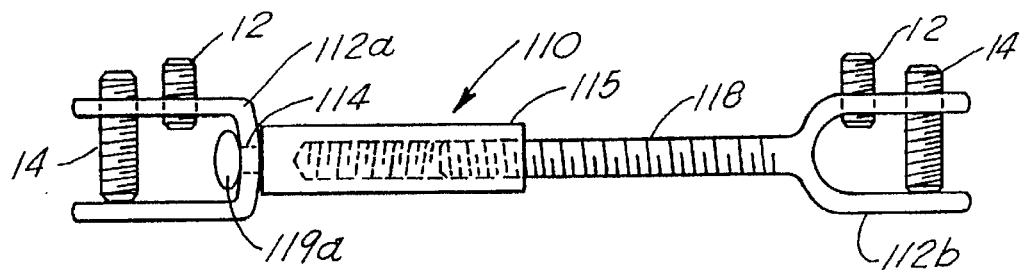
FIG. 11a illustrates a certain embodiment of an adjustable cross bar assembly.
Figure 11B:
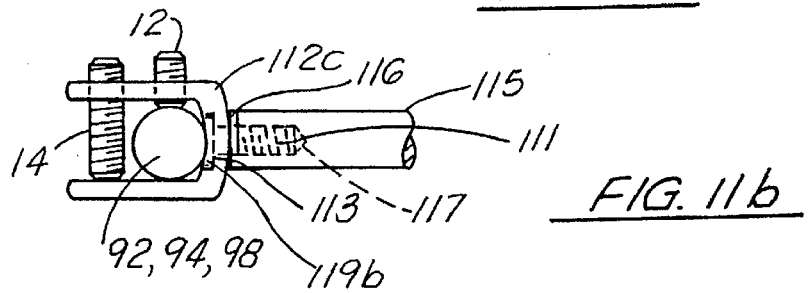
Figure 11C:
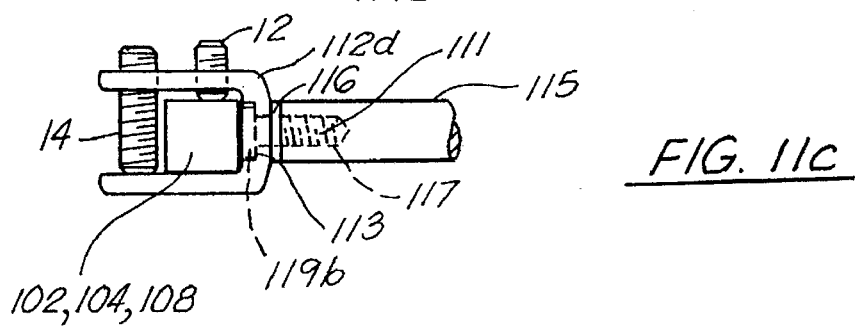
FIG. 11c shows a detail of one end of a certain embodiment of an adjustable cross bar assembly which is configured to accommodate a quadrilateral shaped rod.

In FIG. 1, a spinal fixation system is illustrated showing one of many different potential arrangements of the individual components which are a part of this novel spinal fixation system. The arrangement illustrates one possible combined use of the right-hand double barrel laminar hook 40a, 40b (FIGS. 4, 4a), the single barrel laminar hook 70a, 70b (FIGS. 7a, 7b, 7c), the pedicular bolt clamp assembly 80 (FIGS. 8a, 8c, 8d), the cylindrical rod assembly 90 (FIG. 9) and the adjustable cross bar assembly 110 (FIGS. 11a, 11b, 11c). Note that the double barrel laminar hook 40 (FIGS. 4, 4a) is identical to the double barrel laminar hook 40a, 40b shown installed in FIGS. 1, 2 and 3. Similarly, the single barrel laminar hook 70 (FIGS. 7a, 7b, 7c) is identical to the single barrel laminar hook 70a, 70b shown installed in FIGS. 1, 2 and 3.

Figures 2, 3:
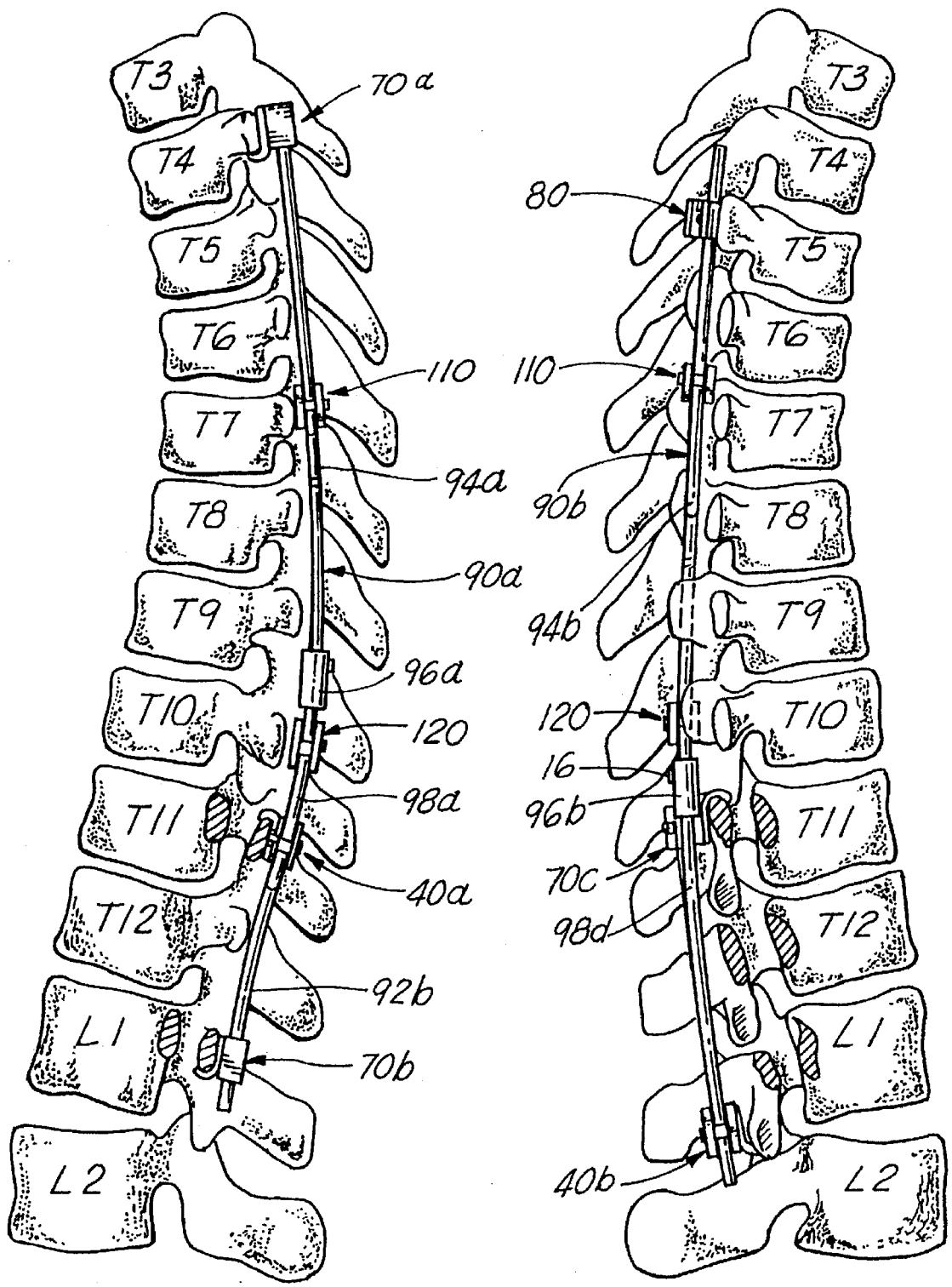
FIG. 2 is a left side view of the left most portion of the embodiment of the present invention shown in FIG. 1.
FIG. 3 is a right side view of the right most portion of the embodiment of the present invention shown in FIG. 1.

Refer now to FIG. 1, a posterior view of a portion of the lumbar and the thoracic spine are illustrated. FIG. 2 illustrates a side view of the spine shown posteriorly in FIG. 1 and also shows the construct installed on the left most side of the spine. On the left most, distal side of the spinal axis, a single barrel laminar hook 70b (FIGS. 7a, 7b, 7c) is shown surgically connected to the inferior border of the lamina of the L1 vertebra. A right-hand double barrel laminar hook 40a (FIG. 4) is shown surgically connected to the superior border of the T11 lamina. A cylindrical rod 92b (FIG. 9) is shown connected to the single barrel laminar hook 70b at one end and the right-hand double barrel laminar hook 40a (FIG. 4) at the other end. The combined assembly of the installed single barrel laminar hook 70b and the right-hand double barrel laminar hook 40a interconnected with the cylindrical rod member 92b creates a clawing action across the L1 and the T11 vertebra. One end of the cylindrical rod member 92b is secured within the bore of the single barrel laminar hook 70b with a set screw 12; while the other end of the cylindrical rod member 92b is secured within the bore of the right-hand double barrel laminar hook 40a with set screw 12a (See FIGS. 4a, 7b).

On the left most proximal side, a single barrel laminar hook 70a (FIGS. 7a,7b,7c) is shown surgically attached to the inferior border of the lamina of the T4 vertebra. The offset cylindrical male rod member 94a, which is one component of the overall cylindrical rod assembly 90 (FIG. 9), is attached to the single barrel laminar hook 70a. The offset cylindrical male rod member 94a is inserted into the cylindrical rod coupler 96a (FIG. 9) and secured therein with at least one (1) rod coupler set screw 16. The cylindrical rod coupler is integral to the straight cylindrical female rod member 98a (FIG. 9) which is secured within the slot of the right-hand double barrel laminar hook 40a (FIG. 4).

Refer now to the right side of the spine in FIG. 1, and to FIG. 3, wherein the spinal construct which is installed on the right most portion of the spine is illustrated. A right-hand double barrel laminar hook 40b (FIG. 4) is shown surgically connected to the inferior border of the lamina of the L1 vertebra. A single barrel laminar hook 70c (FIGS. 7a, 7b, 7c) is shown surgically connected to the superior border of the lamina of the T11 vertebra. The cylindrical rod member 92c (FIG. 9) is interconnected between the single barrel laminar hook 70c and the right-hand double barrel laminar hook 40b. The combined assembly of the installed single barrel laminar hook 70c and the right-hand double barrel laminar hook 40b interconnected with the straight cylindrical male rod member 92c (FIG. 9) creates a clawing action across the L1 and the T11 vertebrae.

One end of the cylindrical rod member 92c is secured within the bore of the single barrel laminar hook 70c with a set screw 12; while the other end of the cylindrical rod member 92c is secured within the bore of the right-hand double barrel laminar hook 40b (FIG. 4) with set screw 12a.

On the top of the right most spinal fixation embodiment, a pedicular bolt clamp 80 (FIG. 8a) is shown installed on the pedicle of the T5 vertebra The pedicular bolt clamp 80 attaches to a previously installed pedicular bolt. The slotted pedicular bolt clamp 85 (FIG. 8b) may also be used in combination with a pedicular bolt and the present invention. A detailed explanation of the operation of the pedicular bolt clamp and the slotted pedicular bolt clamp is included in the pedicular bolt clamp section below. The pedicular bolt clamp 80 is interconnected to the lower right-hand double barrel laminar hook 40b with a cylindrical rod construct 90b (FIG. 9). The cylindrical rod assembly 90b includes an offset cylindrical male rod member 94b which is connected to a straight cylindrical female rod member 98d with a cylindrical rod coupler 96b. The offset cylindrical male rod member 96b is inserted into the cylindrical rod coupler 96 and securely attached with at least one (1) set screw 16. The cylindrical rod assembly 90b is inserted into the slot in the right-hand double barrel laminar hook 40b and the slot 810 in the slotted clamp of the pedicular bolt clamp (see FIG. 8a).

Because the slot 810 is wider than the diameter of the rod members, it is relatively easy to position the rod member within the slot. Precise alignment is generally not necessary. This can reduce the amount of time required for the surgical installation.

An adjustable cross bar assembly 110, (FIG. 11a, 11b, 11c) embodiment of the present invention is illustrated in FIGS. 1,2 and 3 on the upper portion of the construct. On the lower portion of the construct a turnbuckle crossbar assembly is shown. The adjustable cross bar assembly 110a is connected between the individual spinal fixation constructs to provide structural support and rigidity between the constructs. The rotating C-shaped end member 112a of the adjustable cross bar assembly 110a is positioned around the offset cylindrical male rod member 94a and secured to the rod member 94a with set screw 12 (see FIG. 11). Set screw 14 secures the rod member 94a within the interior of the C-shaped end member 112b. The stationary C-shaped end member 112b of the adjustable cross bar assembly 110a is positioned around the offset cylindrical male rod member 94b and secured to the offset cylindrical male rod member 94b with set screw 12. Set screw 14 secures the cylindrical male rod member 94b within the interior of the C-shaped end member 112b.

Similarly, the turnbuckle cross bar assembly 120 (FIG. 12a, 12b) is connected between the straight cylindrical male rod member 98a and the straight cylindrical male rod member 98d. The turnbuckle cross bar assembly 120 may also be used to selectively adjust and secure the spinal fixation constructs shown in FIGS. 1,2 and 3.

The quadrilateral assembly 100 (FIG. 10) may be used instead of the cylindrical rod assembly 90 (FIG. 9). The quadrilateral rods provide torsional stability and help to prevent undesireable rotation and micromotion of the spinal fixation system.

For clarity, Table 1 lists a summary of parts, including the corresponding description and figure numbers.

TABLE 1

PARTS LIST

| Reference Number | Description (FIG. No.) |
| --- | --- |
| 12 | short set screw |
| 14 | long set screw |
| 16 | rod coupler set screw |
| 40 | right-hand double barrel laminar hook (FIGS. 4,4a) |
| 42 | laminar hook |
| 43 | upper leg member |
| 44 | lower leg member |
| 45 | body |
| 46 | slot |
| 48 | bore |
| 50 | left-hand double barrel laminar hook (FIG. 5) |
| 52 | body |
| 60 | right-hand quadrilateral double barrel laminar hook (FIG. 6) |
| 62 | body |
| 64 | square slot |
| 66 | square bore |
| 70 | single barrel hook device (FIGS. 7a,7b,7c) |
| 72 | body |
| 73 | bore |
| 74 | threaded hole |
| 80 | pedicular bolt clamp (FIGS. 8a,8c,8d) |
| 802 | pedicular attaching nut |
| 804 | bore |
| 806 | c-shaped clamp |
| 808 | interdigitating grooves |
| 810 | slot for cylindrical rods |
| 812 | slot for quadrilateral rods |
| 816 | flat region |

TABLE 1-continued

PARTS LIST

| Reference Number | Description (FIG. No.) |
|---|---|
| 818 | interdigitating grooves |
| 820 | inner bore |
| 822 | outer bore |
| 826 | body |
| 88 | pedicular bolt |
| 828 | threaded end |
| 830 | middle portion |
| 832 | upper ledge |
| 85 | slotted pedicular bolt clamp (FIG. 8b) |
| 850 | inner slot |
| 852 | outer slot |
| 854 | slot opening |
| 90 | cylindrical rod assembly (FIG. 9) |
| 92 | straight cylindrical male rod member |
| 94 | offset cylindrical male rod member |
| 96 | cylindrical rod coupler |
| 97 | cylindrical rod coupler pocket |
| 98 | straight cylindrical female rod member |
| 100 | quadrilateral rod assembly (FIG. 10) |
| 102 | straight quadrilateral male rod member |
| 104 | offset quadrilateral male rod member |
| 106 | quadrilateral rod coupler |
| 107 | quadrilateral rod coupler pocket |
| 108 | straight quadrilateral female rod member |
| 110 | adjustable cross bar assembly (FIGS. 11a,11b,11c) |
| 111 | threaded swivel pin |
| 112a | rotating C-shaped end member |
| 112b | stationary C-shaped end member |
| 112c | recessed rotating C-shaped end member |
| 112d | quadrilateral rotating C-shaped end member |
| 113 | countersink |
| 114 | swivel connector |
| 115 | socket member |
| 116 | washer |
| 117 | threaded hole |
| 118 | threaded pin member |
| 119a | oval head member |
| 119b | flat head member |
| 120 | turnbuckle cross bar assembly (FIGS. 12a,12b) |
| 122a | C-shaped end member (left end) |
| 122b | C-shaped end member (right end) |
| 124a | threaded pin member (left end) |
| 124b | threaded pin member (right end) |
| 126 | turnbuckle nut |
| 128 | quadrilateral end member |
| 129 | threaded pin member |

Double barrel laminar hook

Refer now to FIG. 4, wherein an embodiment of the right-hand double barrel laminar hook 40 embodiment of the present invention is shown. The right-hand double barrel laminar hook 40 includes a laminar hook 42, a body 45, an upper leg member 43, a lower leg member 44, short set screws 12a, 12b and a long set screw 14. The laminar hook 42 is attached to the face 43 of the body 45. The laminar hook 42 is arcuate in shape and may be formed with a relatively small or a relatively large radius of curvature. In this way, the overall profile of the hook body 17 or 25 can be kept to a minimum. For example, when the hook is used on the cervical portion of the spine, the radius of curvature can be relatively small but when the hook is used on the thoracic or lumbar portions of the spine, a relatively large radius of curvature may be desired. A variety of different hooks can be made available to be used with the present invention, including, but not limited to hooks that can be used for laminar attachments and hooks that can be used for pedicular attachments. The body 45 includes a bore 48 that is adapted to receive a cylindrical connecting rod 92, 94, 98 (FIG. 9) therethrough. The bore 48 may also be oval in shape to provide the double barrel laminar hook with additional range of movement relative to the cylindrical member during installation.

In FIG. 4a, a bottom view of the right-hand double barrel laminar hook 40 is shown. Two short set screws 12a and 12b are threaded into the side of body 45 wherein the short set screws 12a and 12b engage and secure the side of the cylindrical rods 92, 94, 98 (FIG. 9). The body includes a slot 46 on one end which allows the relatively easy insertion of a cylindrical rod 92, 94, 98 (FIG. 9) therein. The cylindrical rod 92, 94, 98 (FIG. 9) is securely positioned in the base of the slot 46 by rotating the long set screw 14 until it resistively engages against the inside of the opposite fork wall. When the long set screw 14 has been fully rotated clockwise to its innermost position, the cylindrical rod member 92, 94, 98 is still free to move within slot 46 relative to the body 45. The cylindrical rod 92, 94, 98 is securely positioned within the base of the slot 46 by tightening the short set screw 12b. The surgeon may also tighten set screw 12b initially, and subsequently redundantly restrain the rod 92, 94, 98 within slot 46 by rotating set screw 14 fully clockwise.

In FIG. 5, the left-hand double barrel laminar hook 50 embodiment of the present invention is illustrated. The left-hand double barrel laminar hook 50 is essentially identical to the right-hand double barrel laminar hook 40. The left-hand orientation of the left-hand double barrel laminar hook allows the surgeon to position the slot 46, away from the spinal axis during the surgical installation.

Figure 9:
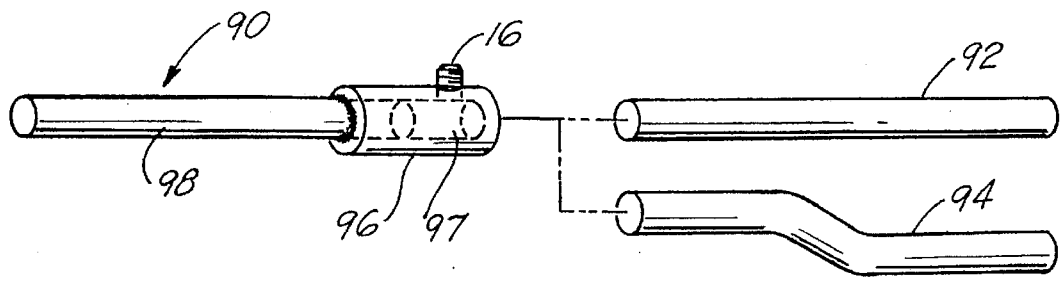
FIG. 9 is an exploded view of a cylindrical rod assembly which shows a female rod and two possible embodiments of interchangeable male cylindrical rod components.
Figure 10:
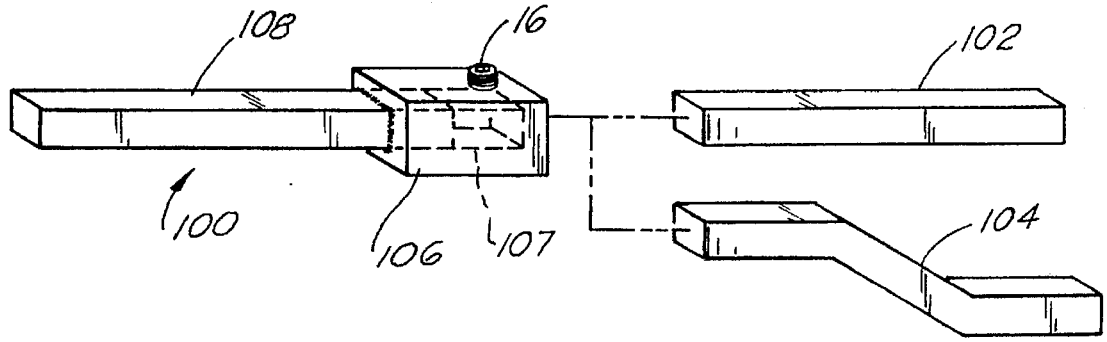
FIG. 10 is an exploded view of a quadrilateral rod assembly which shows a female rod and two possible embodiments of interchangeable male quadrilateral rod components.

In FIG. 6, the quadrilateral right-hand double barrel laminar hook 60 embodiment of the present invention is illustrated. The bore 66 is quadrilateral in cross section to accommodate any of the quadrilateral rods 102, 104, 108 (FIG. 10). The square bore 66 may be larger in the clamping width than the width of the quadrilateral rod to be used thereby allowing a greater range of motion of the quadrilateral double barrel laminar hook 60 relative to the quadrilateral rod during the surgical installation. Although the bore 66 is quadrilateral in cross section, cylindrical rods 92, 94, 98 (FIG. 9) may also be installed in the bore 66.

The square slot 64, also illustrated in FIG. 6, is adapted to receive a quadrilateral rod member 102, 104, 108 (FIG. 10) therein. As with the previously described right-hand double barrel laminar hook 40, the quadrilateral right-hand double barrel laminar hook 60 includes long set screw 14 that is rotated clockwise until it resistively engages against the inside of the opposite fork wall. When the long set screw 14 has been fully rotated clockwise to its innermost position, the quadrilateral rod member 102, 104, 108 (FIG. 10) is still free to move within slot 64 relative to the body 62. The quadrilateral rod member 102, 104, 108 (FIG. 10) is securely positioned within the base of the slot 64 by tightening the short set screw 12b. The surgeon may also tighten set screw 12b initially, and subsequently redundantly restrain the rod 102, 104, 108 within slot 64 by rotating set screw 14 fully clockwise.

Single Barrel Lamainar Hook

In FIGS. 7a, 7b and 7c, a unitary laminar hook clamp 70 embodiment of the present invention is illustrated. The unitary laminar hook clamp 70 includes a body 72 and a laminar hook 42. The body 72 is substantially cylindrical and includes a bore 73 therethrough to receive one of the cylindrical rods 92, 94, 98 (FIG. 9). Bore 73 may also be oval in cross section to provide a greater range of motion of the unitary laminar hook clamp 70 relative to the rod 92, 94, 98 during the surgical installation. Short set screw 12 is threaded into the corresponding threaded hole 74 to engage and firmly secure the outer surface of cylindrical rod 92, 94 or 98. The bore 73 of the unitary laminar hook may also be quadrilateral in shape to correspond to quadrilateral rods 102, 104 or 108 (FIG. 10).

Pedicular Bolt Clamp and Pedicular Bolt

In FIG. 8a, an exploded view of the pedicular bolt clamp 80 embodiment of the present invention is illustrated. The pedicular bolt clamp includes a body 826, a C-shaped clamp 806, a nut 802, a short set screw 12 and a long set screw 14. Also illustrated in FIG. 8a is a pedicular bolt 88. Such a pedicular bolt is shown in U.S. Pat. No. 5,242,443, which is incorporated herein by reference.

The body 826 includes an inner bore 820 and an outer bore 822. The inner bore is sufficiently large in diameter to allow the threaded end 828 of the pedicular bolt 88 to extend therethrough. The diameter of the middle portion 830 of the pedicular bolt 88 is larger than the diameter of the inner bore 820 thereby causing the upper ledge 832 to engage the inner surface between the inner bore 820 and the outer bore 822 of the body 826. The C-shaped clamp 806 includes a bore 804 through which the threaded end 828 of the pedicular bolt 88 extends. The C-shaped clamp also includes interdigitating grooves 808 on the inner surface thereof. The flat region 816 of the body 826 also includes corresponding interdigitating grooves 818. When the C-shaped clamp 806 is positioned on the top of the flat region 816 of the body 826 the interdigitating grooves 808 on the C-shaped clamp are designed to engage the interdigitating grooves 818 of the flat region 816. Furthermore, when the C-shaped clamp 806 is positioned on the top of the flat region 816 of the body 826, the threaded end 828 of the pedicular bolt 88 will extend through the bore 804. The nut 802 is then threaded onto the threaded end 828 of the pedicular bolt 88. Once the body 826 has been oriented to the desired position, the nut 802 is tightened to secure the body 826 to the pedicular bolt. The C-shaped clamp provides a superior compressive bearing surface between the nut 802 and the flat region 816 of the body 826.

In FIG. 8b, a certain slotted pedicular bolt clamp 85 embodiment of the present invention is illustrated. The slotted pedicular bolt clamp 85 is similar in configuration to the pedicular bolt clamp 80. However, a slotted opening 854 having an inner slot 850 and an outer slot 852 is also provided. The inner slot 850 is sufficiently wide to allow the threaded end 828 of the pedicular bolt 88 to extend therethrough. The diameter of the middle portion 830 of the pedicular bolt 88 is larger than the diameter of the inner slot 850 thereby causing the upper ledge 832 to engage the inner surface between the inner slot 850 and the outer slot 852 of the body 826. The slotted opening 854 allows the slotted bolt clamp 85 to be adjusted by positioning the slotted opening 854 at the desired position relative to the pedicular bolt 88. The C-shaped clamp 806, which is described above, is placed on top of the flat region 816 of the body 826. The interdigitating grooves 808 on the C-shaped clamp engage the corresponding interdigitating grooves on the flat region 816 of the body 826. When the C-shaped clamp 806 is in the desired assembled position, the threaded end 828 extends through the slot opening 854 and through the bore 804. The nut 802 is threaded onto the threaded end 828 to secure the pedicular bolt body 826 to the pedicular bolt 88.

Figure 8C:
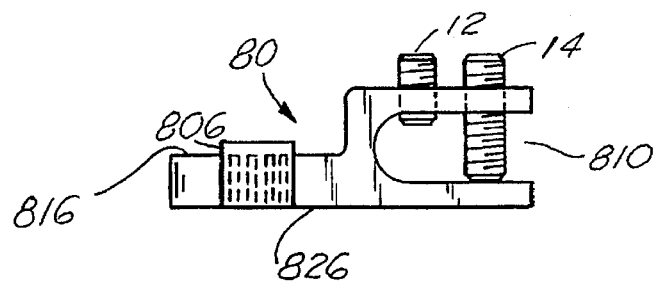
FIG. 8c is a side view of a certain embodiment of the pedicular bolt clamp.

Referring now to FIG. 8c, a side view of the pedicular bolt clamp 80 embodiment of the present invention is illustrated.

Figure 8D:
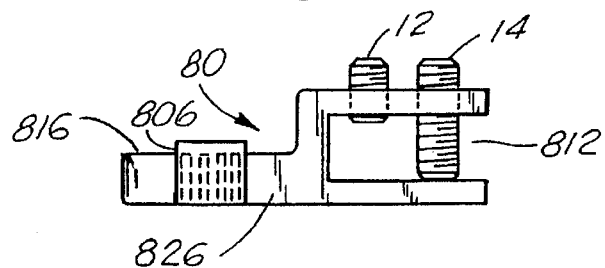
FIG. 8d is a side view of a certain embodiment of the pedicular bolt clamp configured to accommodate a quadrilateral shaped rod.

FIG. 8c illustrates the slot 810 designed to be used with cylindrical rod members (90, 92, 94). In FIG. 8d, a side view of the pedicular bolt clamp 80 is illustrated having a slot 812 designed to be used with quadrilateral rod members (100, 102, 104). The slot configurations shown in FIGS. 8c and 8d may, of course, also be used with the slotted pedicular bolt clamp 85.

Cylindrical and Quadrilateral Rod Assemblies

In FIG. 9, a certain cylindrical rod assembly 90 embodiment of the present invention is illustrated. The cylindrical rod assembly 90 includes a straight cylindrical female rod member 98, a cylindrical rod coupler 96, a straight cylindrical male rod member 92, an offset cylindrical male rod member 94 and a rod coupler set screw 16.

The cylindrical connecting rods 92, 94, 98 (FIG. 9) are typically five or seven millimeters in diameter.

The rod coupler 96 is welded or otherwise coupled to the stationary straight rod member 98. Either the straight cylindrical male rod member 92 or the offset cylindrical male rod member 94 may be inserted into the rod coupler bore 97. Once inserted, the removable cylindrical rod member 92, 94 may be securely attached within the rod coupler by tightening the rod coupler set screw 16 against the outer surface of the cylindrical male rod member 92, 94. It is understood that the lengths of the cylindrical rod members 92, 94 and 98 may be provided in varying lengths to suit the particular surgical requirement. The rod members may also be cut to the appropriate length during the surgical installation procedure.

In FIG. 10, a certain quadrilateral rod assembly 100 embodiment of the present invention is illustrated. The quadrilateral rod assembly 100 is substantially identical to the cylindrical rod assembly 90 which was previously described in detail. The essential difference between quadrilateral rod assembly 100 and the cylindrical rod assembly 90 is the shape of the rod members and rod coupler members. It may be desirable to use quadrilateral members because of the superior torsional characteristics which the quadrilateral members provide.

Adjustable Cross Bar Assembly

In FIG. 11a, an adjustable cross bar assembly 110 embodiment of the present invention is illustrated. The adjustable cross bar assembly 110 includes a rotating C-shaped end member 112a, a swivel connector 114, an oval head member 119a, a socket member 115, a threaded pin member 118, a stationary C-shaped end member 112b, a short set screw 12 and a long set screw 14. The swivel connector 114 is attached to the closed end of the socket member 115 and extends through the base of the rotating C-shaped end member 112a. An oval head member 119a is attached to the end of the swivel connector thereby securing the rotating C-shaped end member 112a to the socket member 115. The socket member 115 may have a knurled outer surface or other engagement surface such as a hexagonal surface for engagement by a wrench.

The threaded pin member 118 engages corresponding threads in the threaded bore of the socket member 115. The stationary C-shaped end member 112b is integral to one end of the threaded pin 118. Both of the C-shaped end members 112a, 112b have a short set screw 12 and a long set screw 14 threaded into one side thereof. Each of the short set screws 12 on the rotating C-shape end member 112a and on the stationary C-shaped end member 112b are used to engage the outside surface of a cylindrical rod member 92, 94, 98 (FIG. 9) or a quadrilateral rod member 102, 104, 108 (FIG. 10). Each of the long set screws 14 on the rotating C-shape end members 112a and on the stationary C-shaped end member 112b are used to secure cylindrical rod member 92, 94, 98 or a quadrilateral rod member 102, 104, 108 within the interior of the respective C-shaped end member 112a, 112b.

In FIG. 11b, an alternative end member embodiment of the present invention is shown. The C-shaped end member 112c includes a countersunk bore 113 in which the head member 119b is positioned. The threaded swivel pin 111 may have a countersunk hex head to engage for tightening. The threaded swivel pin 111 is threaded into the corresponding bore 117. When the threaded swivel pin 111 is fully tightened into the threaded bore 117, a slight gap is created between the head 119b of the threaded swivel pin 111 and the countersunk bore 113. The slight gap allows the C-shaped end member to freely swivel about the threaded swivel pin 111 while the socket member 115 remains stationary. A washer 116 provides a bearing surface between the end of the C-shaped end member 112c and the socket member 115.

In FIG. 11c, a C-shaped end member 112d embodiment of the present invention is shown. The C-shaped end member 112d is substantially identical to the C-shaped end member 112c shown in FIG. 11b. However, the C-shaped end member has orthogonal inner surfaces and 112d is thereby adapted to receive one of the quadrilateral rod members 102, 104 or 108. The quadrilateral rod member 102, 104 or 108 may be secured within the C-shaped end member 112d by tightening the short set screw 12. The quadrilateral rod member 102, 104 or 108 may be further secured by tightening the long set screw 14 until it contacts the inner wall of the opposite leg member as illustrated in FIG. 11c.

Figure 12A:
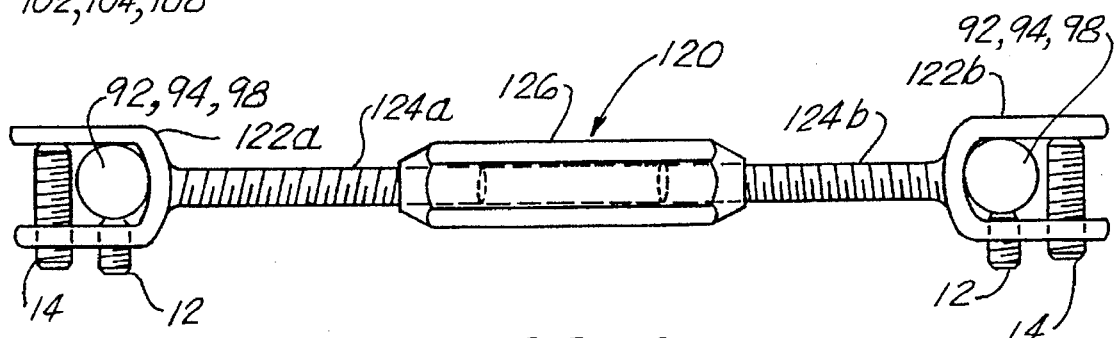
FIG. 12a shows a certain embodiment of a turnbuckle cross bar assembly.

In FIG. 12a, a turnbuckle cross bar assembly 120 embodiment of the present invention is shown. The turnbuckle cross bar assembly 120 includes two (2) C-shaped end members 122a, 122b, two (2) threaded pin members 124a, 124b, a turnbuckle nut 126, a short set screw 12 (one on each end) and a long set screw (one on each end). The C-shaped end member 122a is adapted to receive a cylindrical rod member 92, 94, 98. Both of the C-shaped end members 122a, 122b have a short set screw 12 and a long set screw 14 threaded into one side thereof. Each of the short set screws 12 on the rotating C-shape end members 122a, 122b are used to engage the outside surface of a cylindrical rod member 92, 94, 98 (FIG. 9). Each of the long set screws 14 on the rotating C-shape end members 122a, 122b are used to secure cylindrical rod member 92, 94, 98 within the interior of the respective C-shaped end member 122a, 122b.

The C-shaped end member 122a is integral to the threaded pin 124a. The threaded pin 124a is threaded into one end of the turnbuckle nut 126. Threaded pin 124b is integral to the C-shaped end member 122b. The threaded pin 124b is threaded into the opposite end of the turnbuckle nut 126. Threaded pin 124a and threaded pin 124b have alternate thread directions wherein one of the threaded pins 124a, 124b has a right hand thread, and the other of the threaded pins 124a, 124b has a left hand thread. Similarly, the corresponding turnbuckle nut 126 has right hand threads on one end and left hand threads on the other end. When the threaded pins 124a, 124b have been threaded into the turnbuckle nut 126, a rotation of turnbuckle nut 126 causes the C-shaped end members 122a, 122b to extend or retract, while each C-shaped end member 122a, 122b remains stationary relative to the cylindrical rod member 92, 94, 98.

Figure 12B:
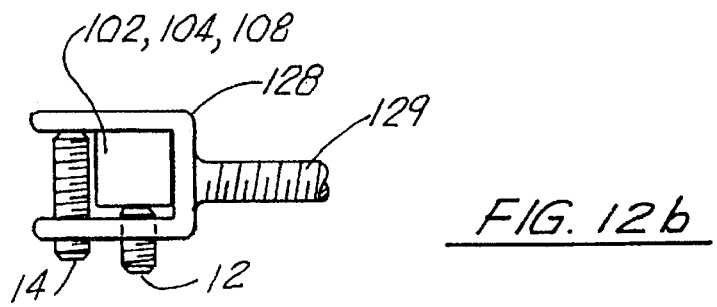

In FIG. 12b, an alternative embodiment of a quadrilateral end member 128 is shown. The quadrilateral end member 128 is configured with an orthogonal internal pocket wherein the quadrilateral end member 129 can be attached to one of the quadrilateral rod members 102, 104, 108. The quadrilateral rod member 102, 104, 108 is secured within the pocket of the quadrilateral end member by tightening the short set screw 12. The quadrilateral rod member 102, 104, 108 is further restrained within the internal pocket by fully tightening the long set screw 14 until the long set screw 14 resistively engages the inside wall of the opposite leg of the quadrilateral end member 129.

The Method

Refer now to all of the figures, and in particular FIGS. 1, 2 and 3, wherein the double barrel spinal fixation system is illustrated which allows the surgeon to construct a rigid, laminal claw that is independent of the rod system. In practicing the method of the present invention, the surgeon follows conventional surgical procedures to expose the effected portion of the spine. The following method description is one possible variation illustrated in FIGS. 1, 2 and 3. It should be understood that the surgeon is free to assemble the spinal construct with individual components described variously herein and assemble the construct in the most desired manner.

A single laminar hook 70 (FIG. 7) is typically surgically attached to the lamina of the selected vertebra. During the attachment, a straight cylindrical male rod member 92 or offset cylindrical male rod member 94 may be loosely inserted into the bore 73 (FIG. 7) of the single laminar hook. A right hand or left hand double barrel laminar hook 40, 50 (FIGS. 4, 5) is then surgically attached to the lamina of the selected vertebra. A right-hand double barrel laminar hook 40a is shown in FIGS. 1 and 2 surgically connected to the lamina of the superior border of the T11 lamina. The cylindrical rod member 92 may be inserted into the bore 48a, 48b of the double barrel laminar hook 40a, 40b either after the double barrel laminar hook has been connected to the desired lamina or prior to the surgical installation.

After the single barrel laminar hook 70 and double barrel laminar hook have been surgically installed, the short set screw 12 on the single barrel laminar hook 70 and the short set screw 12a on the double barrel laminar hook may be tightened to secure the cylindrical rod member to the laminar hooks and to prevent any micromotion across the lamina. The compressire clawing action may be across single lamina or across multiple lamina.

When the clawing of the desired lamina is completed, the surgeon can then proceed with the installation of an additional single barrel laminar hook 70 (FIGS. 7a, 7b, 7c) or a pedicular bolt clamp assembly 80 (FIGS. 8a, 8b, 8c). Following the installation of the additional single barrel laminar hook 70 or pedicular bolt assembly 80, the surgeon can proceed with the reduction and fixation of the spine by connecting a rod assembly 90 (FIG. 9) between the single barrel laminar hook 70 or the pedicular bolt clamp assembly 80 and the double barrel laminar clamp 40, 50.

In FIGS. 1 and 2, a single barrel laminar hook 70a is shown surgically attached to the inferior border of the proximal lamina of the T4 vertebra on the left most concave side of the spine. The cylindrical rod assembly 90a interconnects the single barrel laminar hook 70a and the right-hand double barrel laminar hook 40a. The offset cylindrical male rod member 94a is inserted into the bore 73 of the single barrel laminar hook 70a (FIGS. 7a, 7b, 7c) and secured by tightening the short set screw 12. After fixation and distraction the straight cylindrical female rod member 98a is inserted into the slot 46a of the right-hand double barrel laminar hook 40a (FIG. 4). The short set screw 12b may then be tightened to secure the straight cylindrical female rod member 98a within the slot 46a. The long set screw 14 may then be fully tightened to engage the inside of the opposite inside wall to confine the straight cylindrical female rod member within the slot 46a. Alternatively, the long set screw 14 may be tightened first, securing the rod member within the slot 46a, and subsequently the short set screw 12 may be tightened to secure the rod member to the double barrel clamp. As explained above, the cylindrical rod assembly 90a is comprised of several individual components which may be installed as an assembly or may be installed one piece at a time. This flexible design can save the surgeon time by permitting him or her to complete the connection between the laminar clamps or between a laminar clamp and a pedicular bolt in two stages.

In FIGS. 1 and 3, a pedicular bolt clamp 80 is shown surgically installed on the pedicle of the T5 vertebra on the right most convex side of the spine. The pedicular bolt clamp 80 is installed by first placing the body 826 onto the previously installed pedicular bolt (FIG. 8a, 8b). The threaded end 828 of the pedicular bolt 88 extends through the inner bore 820 whereby the C-shaped clamp 806 may be placed over the body 826. The threaded end 828 then extends through the bore 804 of the C-shaped clamp 806. The interdigitating grooves 808 on the inside surface of the C-shaped clamp 806 engage the interdigitating grooves 818 on the outside of the pedicular bolt clamp 80. The body 826 may be rotated about the pedicular bolt 88 until the desired orientation is achieved. The nut 802 may be attached prior to, or after, the desired orientation is achieved. Once the body 826 is in the desired position, the nut 802 may be tightened with an appropriate wrench.

Alternatively, a slotted pedicular bolt clamp 85 (see FIG. 8b) may be installed on an existing pedicular bolt. The installation of the slotted pedicular bolt clamp 85 is similar to the installation of the pedicular bolt clamp 80. However, the slotted pedicular bolt clamp 85 allows the surgeon to variably position the body 826 relative to the spinal axis. The body 826 of the slotted pedicular bolt clamp 85 is placed onto the previously installed pedicular bolt 88, wherein the threaded end 828 of the pedicular bolt 88 extends through the slot opening 854. The position of the body 826 is then adjusted relative to the spinal axis by positioning threaded end 828 in the desired position within the slotted opening 850. The slotted opening 854 allows the body 826 to be rotated and adjusted laterally relative to the pedicular bolt 88 and the spinal axis. The C-shaped clamp is placed over the threaded end 828 of the pedicular bolt 88 and the nut 802 is threaded onto the threaded end 828 and tightened to the desired torsion. The interdigitating grooves 808 on the inside of the C-shaped clamp engage the interdigitating grooves 818 on the outside of the body 826 to provide a secure assembly.

After the compressive clawing assembly between the right-hand double barrel laminar hook 40b (shown attached to the inferior border of the distal lamina of the L1 vertebra) and the single barrel laminar hook 70c (shown attached to the superior border of the proximal lamina of the T11 vertebra) has been completed, the clawing construct and the pedicular bolt clamp 80 are interconnected with the cylindrical rod assembly 90b (FIG. 9). The offset cylindrical male rod member 94b is inserted into the slot 810 of the pedicular bolt clamp 80 and secured to the pedicular bolt clamp 80 by tightening the short set screw 12 (FIG. 8a). The long set screw 14 is tightened to further secure the rod member within the slot 810. Alternatively, the long set screw may be tightened first, securing the rod within the slot, and subsequently the short set screw may be tightened. This offers the advantage of allowing the rod member to be able to move relative to the pedicular bolt clamp 80 during the reduction and prior to the fixation of the spine.

On the lower end of the cylindrical rod assembly 90b, the straight cylindrical female rod member 98d is inserted into the slot 46a of the right-hand double barrel laminar hook 40b. The rod member is secured within the slot by tightening the short set screw 12 first, and then tightening the long set screw 14. As previously mentioned, the long set screw 14 may be tightened first and then the short set screw may be tightened, depending upon the surgeon's preference.

An adjustable cross bar member is typically installed by the surgeon after the spinal fixation assemblies have been installed. Two (2) adjustable cross bar member embodiments of the present invention are shown in FIGS. 1, 2 and 3. The adjustable cross bar assembly 110 is shown on the upper, thoracic region of the spine. The turnbuckle cross bar assembly 120 is shown on the lower thoracic region of the spine.

Either of the cross bar assemblies 110 or 120 (FIGS. 11a, 11b, 11c, 12a, 12b) may be attached to the rod system at the end of the operative procedure without the need to place the appropriate parts for construction of the cross bar on the rod before the laminar hooks or pedicular clamps are installed. If the adjustable cross bar assembly 110 is being used, the C-shaped end members 112a and 112b are positioned around the longitudinal or quadrilateral rods which are being used in the spinal fixation system. Subsequently, the long set screws 14 are tightened to secure the C-shaped end members onto the corresponding rod members. The socket member is adjusted with a corresponding nut or pliers to achieve the desired degree of separation or tension between the longitudinal rod constructs positioned on each side of the spine. Once the adjustable cross bar assembly 110 is properly adjusted, the short set screws are tightened against the longitudinal cylindrical or quadrilateral members. The overall structure prevents micromotion between the vertebra, and between the individual components of the assembly. The overall structure also helps to provide torsional stability. The socket member 115 may also be secured to the threaded pin member with a cotter pin or other restraining device.

The turnbuckle cross bar assembly 120 is installed in essentially the same manner as the adjustable cross bar assembly 110. However, the turnbuckle cross bar assembly 120 is adjusted between the cylindrical or quadrilateral longitudinal members by rotating the turnbuckle nut clockwise or counterclockwise until the desired separation and tension between the longitudinal members is achieved. The nut 126 may also be secured to one or both of the threaded pin members 124a, 124b with a cotter pin, or other restraining device.

Because many varying and different embodiments may be made within the scope of the inventive concept herein taught, and because many modifications may be made in the embodiments herein detailed in accordance with the descriptive requirement of the law, it is to be understood that the details herein disclosed are to be interpreted as illustrative and not in a limiting sense. Moreover, it is to be understood that the present inventive concept may be used to assist with the correction of many varied diseases of the spine including but not limited to fractures, dislocations and other physiological abnormalities.

What is claimed is:

1. A surgically installed spinal fixation system comprising:
   (a) a body member having two generally parallel faces and a first opening therethrough adapted to receive a first longitudinal member; the centerline of said first opening is positioned generally along a spinal axis;
   (b) said body member also having a slotted second opening is positioned generally along said spinal axis whereby a second longitudinal member can be inserted into said slotted second opening;
   (c) a hook member connected to the outer surface of one of said generally parallel faces;
   (d) means for securing the outer surface of said first longitudinal member to the body member;
   (e) means for securing the outer surface of said second longitudinal member to the body member.

2. A surgically installed spinal fixation system as claimed in claim 1 wherein said first opening has a circular cross section.

3. A surgically installed spinal fixation system as claimed in claim 1 wherein said first opening has a quadrilateral cross section.

4. A spinal fixation system as claimed in claim 1 wherein at least one said body member is surgically installed on each side of the spine.

5. A spinal fixation system as claimed in claim 4, wherein said longitudinal members are separated by an adjustment means for selectively spacing said second longitudinal members.

6. A spinal fixation system as claimed in claim 4, wherein said adjustment means has two bifurcated ends adapted to engage said second longitudinal members; said bifurcated ends being separated by a linearly adjustable coupler therebetween; each said bifurcated end having two forks; one of each said forks having an engagement member for engaging at least one wall of each of said longitudinal members.

7. A spinal fixation system as claimed in claim 1, including at least two of said body members which are adapted to be surgically installed together with two of said longitudinal members; and each of said longitudinal members being separated by an adjustment means for selectively adjusting the distance between said longitudinal members;
   (a) said adjustment means having two bifurcated ends adapted to engage said longitudinal members;
   (b) said bifurcated ends being separated by a linearly adjustable threaded coupler therebetween;
   (c) each said bifurcated end having two forks; one of each said forks having an engagement means for engaging at least one wall of each of said longitudinal members.

8. A surgically installed spinal fixation system comprising:
   (a) a body member having a first leg member and a second leg member and a slotted opening therebetween for receiving a first longitudinal member laterally into said slotted opening;
   (b) said first leg member having a first engagement means for engaging the outer surface of said first longitudinal member; and
   (c) said first leg member further having a second engagement means for engaging the outer surface of said first longitudinal members.

9. The system of claim 8, wherein said body member includes a body extension from said first and second leg members having a aperture therethrough; and a pedicular screw adapted to secure a second longitudinal member in said bore.

10. A surgically installed spinal fixation system as claimed in claim 9, wherein said first leg member is further adapted to receive a restraining means for restraining said first longitudinal member; said restraining member extends through said first leg member and along at least one side of said first longitudinal member.

11. A surgically installed spinal fixation system as claimed in claim 9, wherein said body extension has a substantially flat end with an outer surface having a first set of interdigitating splines; a substantially C-shaped member having an inner surface with a second set of interdigitating splines whereby said second set of interdigitating splines engages said first set of interdigitating splines; and a connecting means positioned above said C-shaped member for engaging said pedicular screw whereby said connecting means provides compression between said body member and said pedicular screw.

12. A spinal fixation system comprising:
   (a) a clamping means having a through bore with a center line positioned substantially parallel to the spinal axis and a slot having a center line aligned substantially parallel with said spinal axis;
   (b) a first interconnecting means for interconnecting at least two said clamping means;
   (c) a second interconnecting means for interconnecting one of said at least two clamping means to at least one other said clamping means.

13. A spinal fixation system as claimed in claim 12, wherein at least one said spinal fixation system is positioned on each side of said spinal axis.

14. A spinal fixation system as claimed in claim 13, further comprising an adjustment means for selectively adjusting the distance between each of said second interconnecting means.

15. A spinal fixation system as claimed in claim 14, wherein said interconnecting means is cylindrical.

16. A spinal fixation system as claimed in claim 14, wherein said interconnecting means is quadrilateral.

17. An apparatus for selectively separating surgically installed longitudinal members comprising:
   A first C-shaped member having a bore positioned at the base thereof; said bore adapted to rotatably receive a first elongated member having a threaded bore; A second elongated member having a threaded pin portion on one end and a second C-shaped member on the other end; said threaded pin portion adjustably threaded into said threaded bore of said first elongated member; whereby the distance between said first C-shaped member and said second C-shaped member can be selectively adjusted by rotating said first elongated member.

18. An apparatus as claimed in claim 17, wherein each of said C-shaped members define an internal radial pocket; said C-shaped members further having means for securing an elongated member within said internal radial pocket.

19. A method of constructing a rigid laminal claw independent of the spinal rod system to correct a spinal deformity comprising the steps of:
   (a) surgically exposing the spine posteriorly;
   (b) clawing single or multiple lamina by interconnecting at least two clawing means for attaching to the spine;
   (c) reducing and fixating the deformity of the spine by attaching said at least two clawing means to a longitudinal member extending generally along the spine; and
   (d) attaching at least one end of said longitudinal member to the spine with a combination pedicular screw and clamping member.

20. A method of constructing a rigid laminal claw as claimed in claim 19, wherein each of said steps a, b, c and d is performed on each side of the spine.

21. A method of constructing a rigid laminal claw as claimed in claim 20, including the additional step of attaching adjustment means for adjusting the distance between each of said longitudinal members.

22. A method of constructing a rigid laminal claw independent of the spinal rod system to correct a spinal deformity comprising the steps of:

(a) surgically exposing the spine posteriorly;

(b) clawing single or multiple lamina by interconnecting at least two clawing means for attaching to the spine;

(c) reducing and fixating the deformity of the spine by attaching said at least two clawing means to a longitudinal member extending generally along the spine; and (d) attaching said clawing means to said spine with a combination laminar hook and clamping member.

23. A method of constructing a rigid laminal claw as claimed in claim 22, wherein each of said steps a, b, c and d is performed on each side of the spine.

24. A method of constructing a rigid laminal claw as claimed in claim 23, including the additional step of attaching adjustment means for adjusting the distance between each of said longitudinal members.

* * * * *